United States Patent [19]

Skeens et al.

[11] Patent Number: 5,464,410
[45] Date of Patent: * Nov. 7, 1995

[54] IMAGING FIXATION AND LOCALIZATION SYSTEM WITH RESPIRATORY FEEDBACK DEVICE

[75] Inventors: Joseph L. Skeens; Linda M. Miketic, both of Pittsburgh, Pa.

[73] Assignee: University of Pittsburgh, Pittsburgh, Pa.

[*] Notice: The portion of the term of this patent subsequent to Sep. 7, 2010, has been disclaimed.

[21] Appl. No.: 909,310

[22] Filed: Jul. 6, 1992

Related U.S. Application Data

[62] Division of Ser. No. 695,687, May 3, 1991, Pat. No. 5,242,455.

[51] Int. Cl.$^6$ .................................................... A61B 19/00
[52] U.S. Cl. ............................................ 606/130; 128/725
[58] Field of Search ................... 606/130; 128/720–728, 128/653 R, 653 A, 653 SC, 200.24, 716, 719

[56] References Cited

U.S. PATENT DOCUMENTS

| | | | |
|---|---|---|---|
| 3,818,901 | 6/1974 | Sanctuary et al. | 128/719 |
| 3,962,917 | 7/1976 | Terada | 128/724 |
| 3,991,304 | 11/1976 | Hillsman | 128/725 |
| 4,036,217 | 7/1977 | Ito et al. | 128/723 |
| 4,221,381 | 9/1980 | Ericson | 128/727 |
| 4,269,196 | 5/1981 | Toms et al. | 128/727 |
| 4,323,078 | 4/1982 | Heimlich | 128/728 |
| 4,406,291 | 9/1983 | Schwesinger | 128/728 |
| 4,499,905 | 2/1985 | Greenberg et al. | 128/727 |
| 4,583,538 | 4/1986 | Onik et al. | 606/130 |
| 4,665,926 | 5/1987 | Leuner et al. | 128/727 |
| 4,706,685 | 11/1987 | Jones et al. | 128/725 |
| 4,784,083 | 8/1981 | Lester | 128/725 |
| 4,905,699 | 3/1990 | Sano et al. | 128/721 |
| 5,242,455 | 9/1993 | Skeens et al. | 606/130 |

Primary Examiner—Stephen C. Pellegrino
Assistant Examiner—Glenn Dawson
Attorney, Agent, or Firm—Reed Smith Shaw & McClay

[57] ABSTRACT

The present invention relates to a method and apparatus for lesion localization and stereotactic placement of probes into the body utilizing an imaging system. Localization of the probe with reference to the device itself is accomplished by providing a base which includes a base localization grid and at least one localizing side member which includes a side localization grid. Extremely accurate placement of the probe within the body is accomplished by providing a spanning member to which a probe holder is attached. The spanning member is designed so as to be attachable to the base at any angle in the sagittal plane with respect to the base. The stereotactic device also includes a precompression device to compress soft tissue in the area of the probe entry point before penetration. A respiration feedback device which directly measures respiratory volume is also provided to enable a patient to control the patient's degree of respiration. The feedback device can thus ensure that each scan is taken in the same phase of respiration.

21 Claims, 9 Drawing Sheets

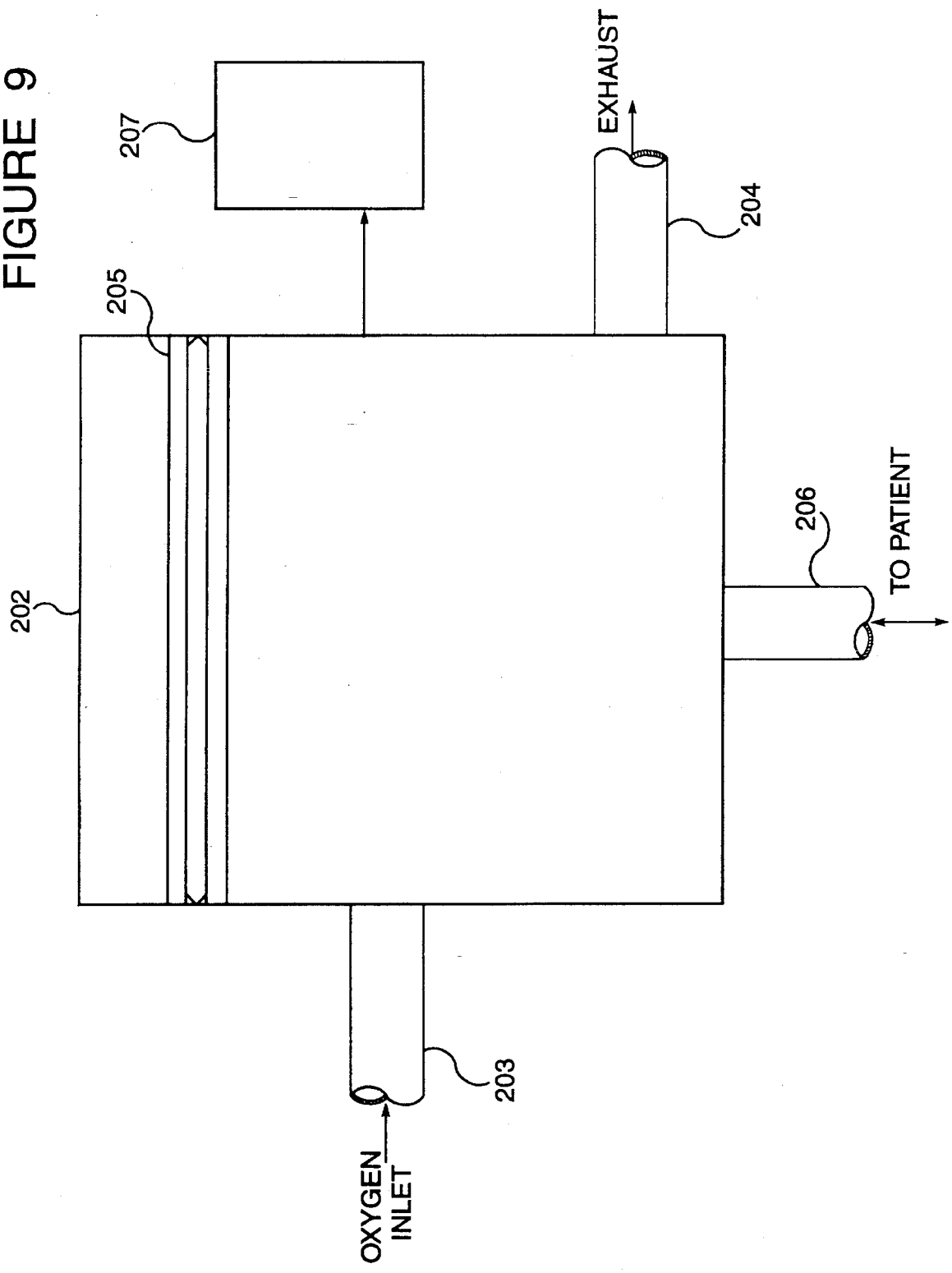

IMAGING FIXATION AND LOCALIZATION SYSTEM WITH RESPIRATORY FEEDBACK DEVICE

This is a divisional of application Ser. No. 07/695,687 filed on May 3, 1991, now U.S. Pat. No. 5,242,455.

FIELD OF THE INVENTION

The invention relates to a method and apparatus for lesion localization and stereotactic placement of probes into the body utilizing imaging systems such as magnetic resonance imaging ("MRI") or computerized tomography (CT), and, in particular, to a method and apparatus for the stereotactic placement of biopsy needles with high accuracy.

BACKGROUND OF THE INVENTION

Computerized axial tomography ("CAT") or computerized tomography images an axial section of a patient by obtaining a series of different angular projections of the section and reconstructing a two-dimensional image from the series of one-dimensional projections. In contrast to conventional tomography and radiology, x-rays do not pass through the adjacent anatomy, only through the section of interest.

Contemporary scanners are of the third- or fourth-generation variety. The third-generation design is a "rotate-rotate" scanner, in which the tube and detector array are directed opposite each other and are both rotatable movable around the patient. The fourth-generation systems rotate the x-ray tube, but keep the detector array stationary.

With the advent of third and fourth-generation CT scanners, invasive and interventional procedures that are performed under CT guidance are now used extensively. CT-guided needle aspiration biopsies have been highly successful and have alleviated the need for diagnostic surgery in many cases. In addition, CT now guides the percutaneous drainage of abdominal abscesses, reducing the need for repeated surgery. Until recently, however, all of these procedures were guided manually, causing the process to be time consuming and also requiring multiple needle manipulations and repeat scannings to verify needle placement.

Magnetic Resonance Imaging, MRI, is a method of using low energy electromagnetic radiation rather than high energy x-rays to produce diagnostic medical images. By varying magnetic fields and the emission of radio waves, signals can be produced and reconstructed into two or three dimensional images. MRI technology is commonly used to provide information in a format similar to computed axial tomography but with unique flexibility in choosing the reconstruction plane. Equipment used with a magnetic resonance scanner must be nonferromagnetic so as not to interfere with its operation.

There are certain medical conditions, such as some types of metastatic liver cancer, that can be evaluated only with MRI. Furthermore, because of anatomic considerations, different planes than the axial may be needed to direct biopsies. No existing biopsy device meets the three dimensional or nonferromagnetic needs of MRI directed procedures.

CT stereotaxis is a well-established procedure for the head. The bony skull, with its consistent relationship to the brain, allows attachment of a rigid frame. In such devices, reference coordinates from which various entry paths are calculated are taken from the attached frame itself rather than from the patient's skin.

In *CT-Guided Stereotaxic Biopsy Of Brain Tumors: New Technology For An Old Problem,* H. Black, A. Mechanic and R. Markowitz, 10(4) Am. J. Clin. Oncol. 285 (1987), for example, a metal base ring for fixation to the skull with localizing rings consisting of carbon fiber rods arranged vertically and diagonally is disclosed. The carbon rods of the localization rings appear on the CT scan to enable localization of the lesion. The biopsy probe-carrier is attached to an arc guidance system which is applied to the base ring fixed upon the patient's head. The arc system enables positioning of the probe at any angle in a single plane.

In *Preliminary Experience With Brown-Roberts-Wells (BRW) Computerized Tomography Stereotaxic Guidance System,* P. Heilbrun, T. S. Roberts, M. L. J. Apuzzo, T. H. Wells, and J. K. Sabshin, 59 J. Neurosurg. 217 (1983), a stereotactic system consisting of a head ring, a localization system, an arc guidance system, a phantom simulator, and a forstan are disclosed for use in stereotaxic guidance on the skull.

U.S. Pat. No. 4,463,758 discloses a stereotactic frame designed for use with a CT scanner. The frame comprises a platform including an area for supporting a patient's head and for maintaining the patient's head in position. The support is provided with pins that may be threadably extended to engage the patient's head. An inverted, substantially U-shaped frame is pivotally mounted on the support. A probe holder is movably mounted on either the leg portion of the U-shaped frame or the base portion of the U-shaped frame.

In U.S. Pat. No. 4,592,352, an apparatus for performing surgical procedures through a patient's skull to a target within the skull by utilizing CT and NMR scanners is disclosed. The apparatus includes a base platform and a pair of vertical support members on opposite sides of the base platform. A head holder is mounted on the base platform to accommodate the patient's head. The head holder includes screws that extend inwardly therefrom for engaging the patient's skull. An arc carrier is pivotally mounted to arc carrier supports and has an arcward segment movably mounted thereon. A probe holder is further selectively mounted on the arc carrier. The apparatus is free of artifact and may be moved to any desired angle. The probe holder on the arc carrier may be rotated to any desired angle so as to reach the target through any point on the skull.

Unlike the skull, the body does not have a consistent relationship of its surface anatomy to the underlying organs. Many of the organs within the thorax and abdominal cavities move with respiration so that changes in the phases of respiration affect the spatial relationship of organs to the superficial soft tissue. Furthermore, there is no structure to which a rigid frame can be attached.

A handheld guidance device for use in conjunction with a CT scanner which allows a user to place a probe within a patient's body at a desired angle is disclosed in U.S. Pat. No. 4,733,661. The guidance device includes a generally planar base including a bubble level to aid in maintaining the base horizontal. A needle support arm is pivotally attached to the base. A cooperating protractor indicates the relative angle of the needle in relation to the base. The accuracy of probe placement obtainable with such a handheld device is severely limited, however.

U.S. Pat. No. 4,583,538 discloses a method and apparatus allowing CT guided biopsies of the body. The method is based upon finding a reference point on the patient's body that exactly correlates to a point on the CT scanner. Locating the reference point is accomplished by means of a localization device placed on the patient's skin. The localization device can be identified in the cross-section of a CT scan. Measurement of the localization device on the CT scanner is then correlated to the device on the patient.

A device which allows angular rotations about the X, Y and Z axes to enable any orientation of the needle direction to be set for penetration is also disclosed. The device has two moving members that provide displacements in the Y-axis direction. X-axis movement is accomplished by an X-travel bar and Z-axis movement is accomplished by a Z-travel bar. Angular rotations about these axis enable any orientation of a needle direction to be set for successful guidance to a target. The multiple axes of such a device maximize torsion within the system, however, thereby severely limiting the accuracy of needle placement. The stability of the system is also decreased because the force applied to the probe is tangential to the support. Stability and reproducibility are especially essential in MRI applications. An additional source of inaccuracy arises in that the interface of the device with the biopsy needle does not allow constant guidance into the target.

In an attempt to address the problem of the change in spatial relationship of internal organs of the body to the superficial soft tissue with change in the phase of respiration, U.S. Pat. No. 4,583,538 discloses a respiratory gating device. The gating device employs a water and tube strain gage that is wrapped around a patient's chest and subsequently connected to a transducer. The transducer gives a digital representation of the patient's phase of respiration. This indirect measurement of respiratory volume introduces significant error, however, which can result in the need for multiple needle insertions to successfully localize a mass lesion. A major source of such error is the vast number of forms and sizes the human chest may take.

Inaccuracy in depth measurement of a biopsy needle as a result of soft tissue compression is another problem experienced with current stereotactic procedures performed on areas of body other than the head. Error from soft tissue compression in combination with the variation in axial position resulting from respiratory variation can result in the need for multiple needle insertions even with CT or MRI guidance using current stereotactic procedures. Multiple needle insertions increase the risk of bleeding and infection as well as the risk of inadvertent puncture of other internal organs and vascular structures. Improper needle localization in the chest, for example, can cause partial or complete collapse of a lung.

Still a further problem in current stereotactic procedures is the difficulty in maintaining the needle and lesion in the same plane of a CT or MRI section. This can result in the over-utilization of time to locate the tip of the biopsy needle to ensure that the biopsy needle has penetrated the lesion, thereby increasing both medical costs and patient anxiety. Additionally, complex approximation of angles within the plane of section result in further over-utilization of time and increase the likelihood of error.

Still a further problem encountered with MRI stereotactic applications is the need to provide greater accuracy and to reduce the scanner time required. In MRI applications, realignment of the needle and confirmation of its position can require impractical periods of time if not done efficiently.

Accordingly, an object of the present invention is to provide a stereotactic biopsy device that eliminates or minimizes the above problems while imparting a greater level of physician confidence in interpreting biopsy results.

SUMMARY OF THE INVENTION

Generally, the present invention is a stereotactic localization device for use in conjunction with an imaging guidance system to place a probe within a human body comprising a base including a base localization grid, at least one localizing side member including a side localization grid, a spanning member capable of spanning the base localization grid, a means for positioning the spanning member to span the base and enabling orientation of the spanning member at a predetermined angle and height with respect to the base. The predetermined angle of the spanning member with respect to the base is defined by an image plane of the imaging guidance system in which a target for placement of the probe lies. The height of the spanning member with respect to the base is adjustable to minimize the distance between the spanning member and the body. The stereotactic localization device further comprises a means for holding the probe being rotatable within the image plane to enable orientation of the probe at a desired angle within the image plane, a means positioned on the spanning member for attaching the probe holding means to the spanning member at a defined position thereon, and a protractor means disposed adjacent to the probe holding means to enable rapid determination of the orientation of the probe.

The present device provides the stability and reproductibility that are required to achieve accurate placement of probes such as biopsy/drainage needles using imaging system guidance including both CT and MRI guidance. A degree of accuracy of less than 1.0 mm of variance at a penetration depth of 23.0 cm is easily obtainable with the present invention. An accuracy of 0.2 mm at a penetration depth of 23.0 cm is achievable under conditions of ideal construction and homogeneous tissue.

For many biopsies it is simply desired to insert the probe perpendicular to the table, and in those cases where angulation is needed it is only desirable to adjust the angle of the probe within the image plane. If one angles the probe through more than one image plane, it becomes difficult to determine the exact location of the probe tip. By orienting the spanning member at an angle with respect to the base corresponding to the angle of the image plane with respect to said base so that the probe lies within the image plane and allowing rotation of the probe only within the image plane, the present device maintains the entire probe within the same image plane, thereby simplifying confirmation of probe placement in subsequent images. The degrees of freedom available to the device must, therefore, be within the plane of the image constructed by the imaging system scanner. In other words, regardless of how the device is manipulated, the entire length of the biopsy needle is always in the plane of the image.

Because the device is scanned along with the patient, it must be manufactured from a material that is substantially transparent to the form of energy utilized in constructing the image. To maintain positional accuracy, the construction materials also preferably have a high stiffness. Therefore, relatively low-radiodensity, high-stiffness, nonferromagnetic materials are preferably used. Aluminum and certain plastics are well suited for both CT and MRI applications.

The stereotactic localization device preferably includes precompression means to compress in a controlled manner soft tissue in the area of the probe entry point before penetration. The precompression means thereby minimizes mislocation of the biopsy needle resulting from soft tissue compression.

The stereotactic localization device also preferably includes a respiration feedback means which directly measures respiratory volume to define a phase of respiration. The respiratory feedback means is adapted to enable a patient upon whom a biopsy or a diagnostic examination is being performed to control the patient's degree of respirations.

The present approach differs greatly from previously known respiratory gating devices used in CT guided biopsies in that it is proposed to directly measure the respiratory volume with instantaneous visual, auditory and/or tactile information available to the patient and operator to serve as feedback. Every image slice can thereby be obtained in the same phase of respiration and the effects of respiration on the accuracy of probe placement thereby minimized. Additionally, the phase of respiration is preferably displayed on each image obtained.

BRIEF DESCRIPTION OF THE DRAWINGS

FIG. 9 is a diagram of the constant volume chamber.

PRESENTLY PREFERRED EMBODIMENT

Figure 1:
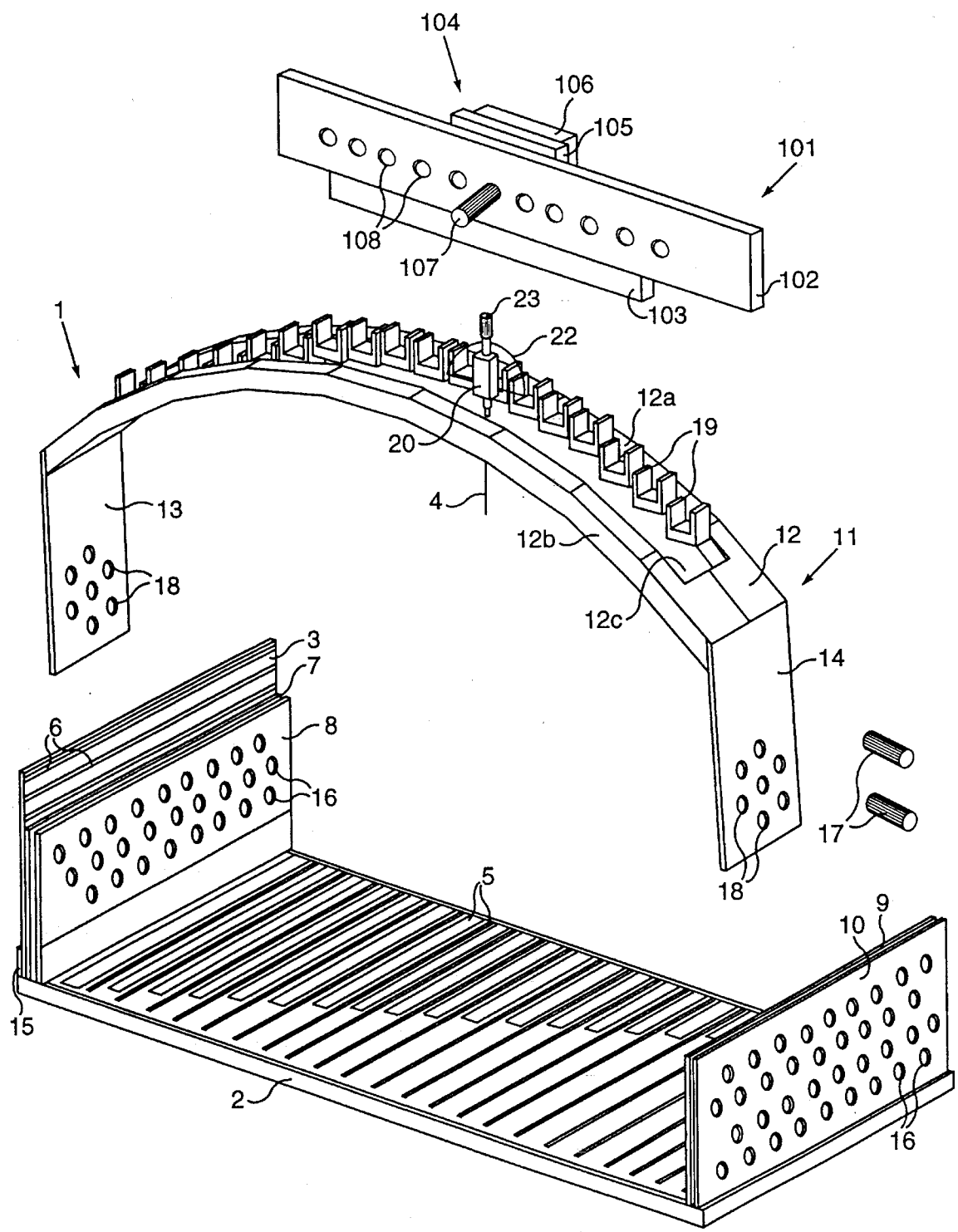
FIG. 1 is right hand perspective view of the device.

The device 1 as shown in FIG. 1 comprises a base 2 and at least one localizing side member 3 preferably removably attached to base 2. Localizing side member 3 may also be positioned adjacent base 2. In any event, localizing side member 3 is preferably positioned at a known angle with respect to base 2 and most preferably positioned orthoganally with respect to base 2. Because device 1 is located in the plane of section during imaging, it must be constructed of materials which are substantially transparent to the form of energy utilized to construct the image. To ensure that the entry point and path remain constant during biopsy or other invasive procedure, these materials must also be of adequate stiffness to prevent deflection under loads normally experienced during the procedure.

Materials are typically given attenuation coefficients corresponding to their radiodensities. The attenuation coefficients may be arranged on a scale from negative to positive 1,000, known as the Hounsfield scale, in which −1,000 is the attenuation coefficient in air, zero is the attenuation coefficient for water, and +1,000 is the attenuation coefficient for dense bone. Preferably, for CT application, the construction materials chosen for use in device 1 have relatively low radiodensities with attenuation coefficients in the range of approximately −100 to +100 Hounsfield units. The construction materials are also preferably nonferromagnetic for MRI applications. Certain plastics and aluminum are examples of nonferromagnetic materials having suitable attenuation coefficients.

Figure 2:
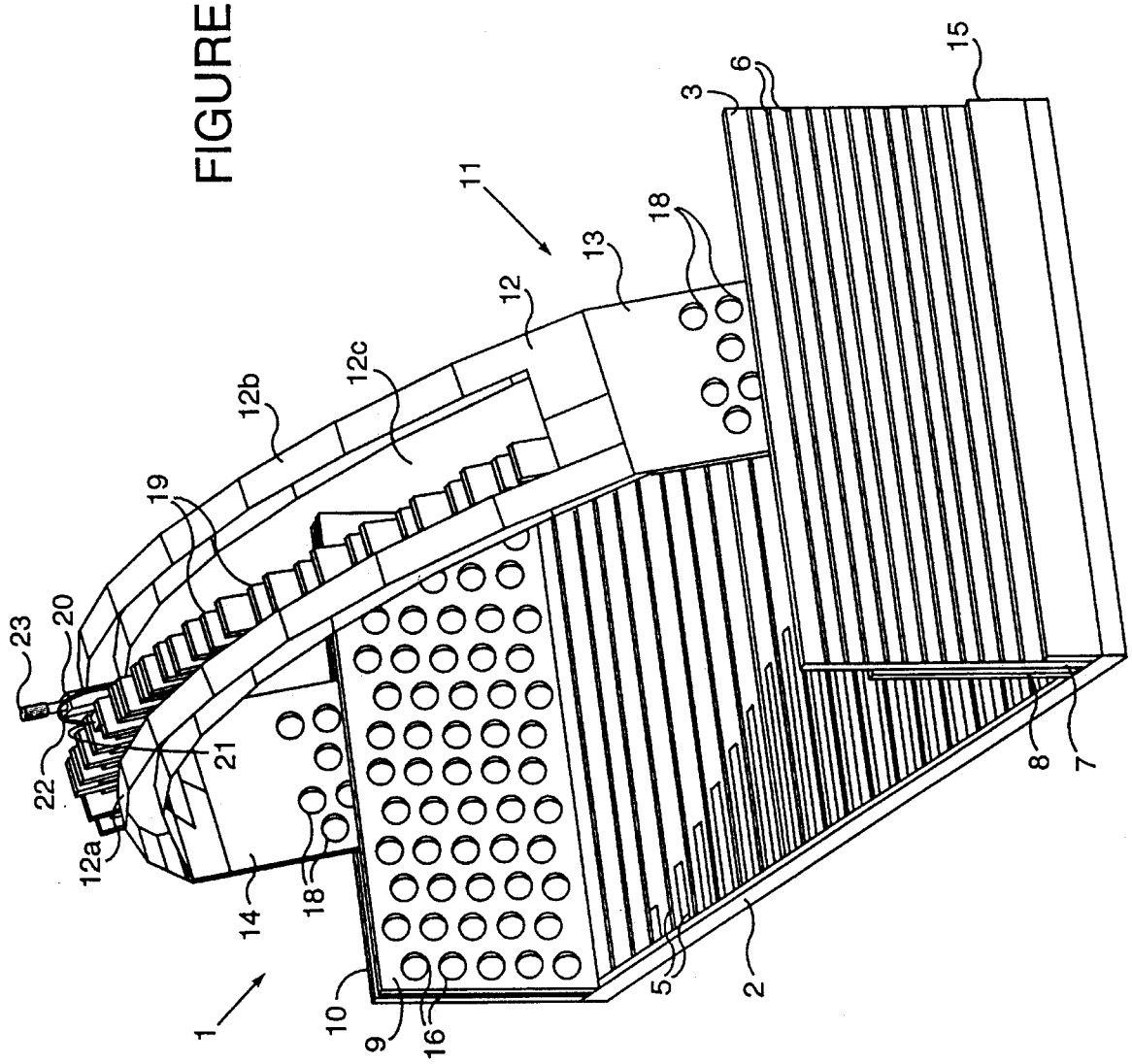
FIG. 2 is a left hand perspective view of the device showing the spanning member oriented at an oblique angle.

By locating stereotactic localization device 1 and the tumor or lesion in the image section, the lesion can be referenced to the external features of device 1. In this manner, the tip of penetration means or probe 4 may be quickly placed in position, and the depth of penetration promptly determined. Therefore, base 2 and localizing side member 3 are equipped with localization grids 5 and 6, respectively. Side localization grid 6 is best depicted in FIG. 2. Preferably, base localization grid 5 and side localization grid 6 comprise accurately and regularly spaced radiopaque segments which are mounted through localizing side member 3 and base 2.

The relatively radiopaque segments (as compared to the radiodensity of the primary construction materials) of localization grids 5 and 6 appear clearly on the CT or MRI scan. The small size and low density of the radiopaque segments of localization grids 5 and 6 relative to tissue prevent the formation of artifacts in the image. The position of the lesion and the needle tip position may thus be determined with respect to the frame by examining the imaging system scan. An example of a suitable material for the radiopage segments of localization grids 5 and 6 for CT or MRI applications is copper.

On each lateral side of the base 2, support members 7, 8, 9, and 10 are preferably provided so that a spanning member 11 can be positioned appropriately with respect to base 2. Preferably, two such support members 7 and 8 are attached parallel to each other on one lateral side of base 2 and two other support members 9 and 10 are attached parallel to each other on the other lateral side of base 2. Spanning member 11 preferably comprises a spanning frame section 12 and two lateral frame sections 13 and 14. One of lateral frame sections 13 and 14 is preferably attached to each lateral side of spanning frame section 12.

Localizing side member 3 is preferably made removably attachable to base 2. Base 2 is thus preferably equipped with abutment means 15 rigidly attached thereto. Abutment means 15 is preferably attached to base 2 at a defined distance from support member 7 and parallel to support member 7 so that vertical localization member 3 can be slid between abutment means 15 and support member 7 and firmly but removably held in place.

Figure 3:
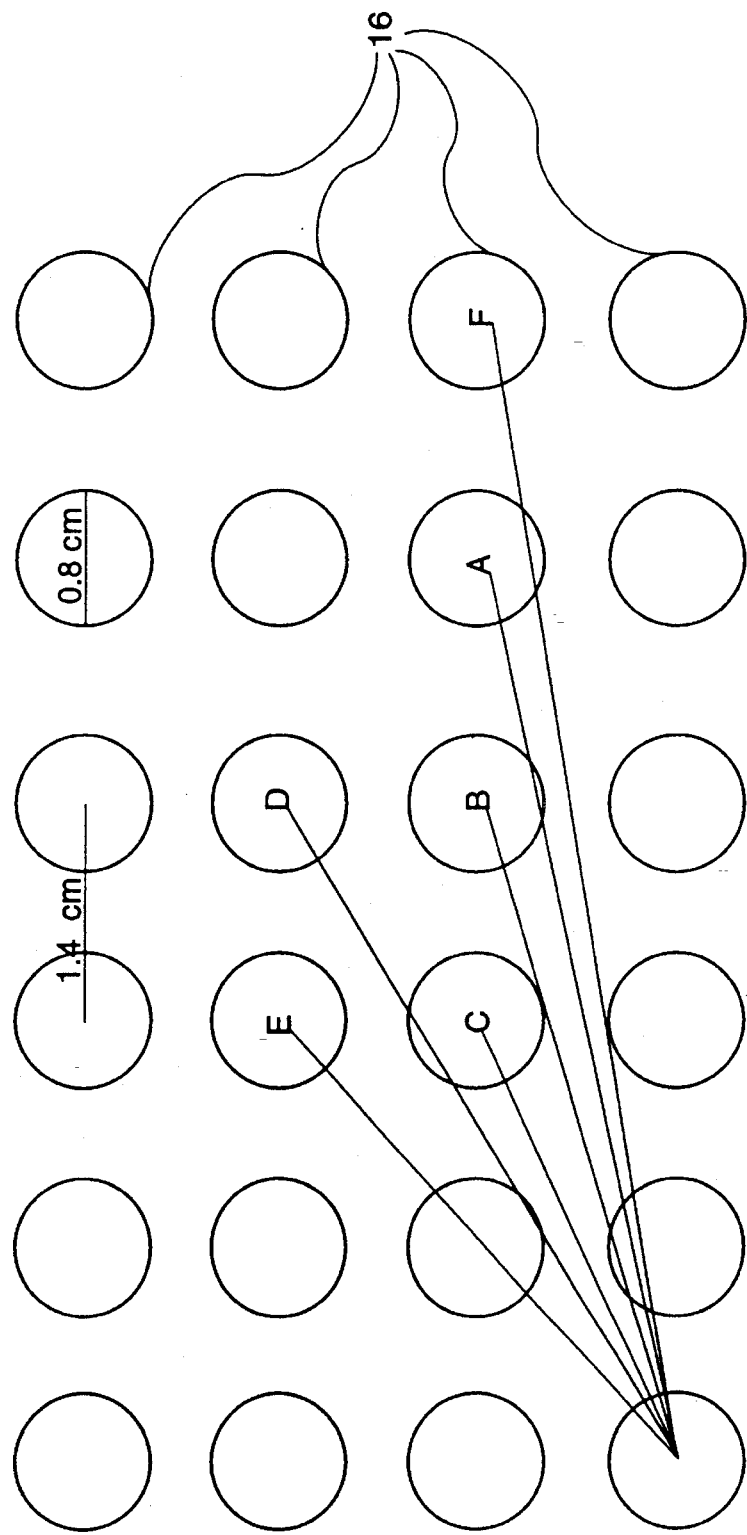
FIG. 3 is a schematic diagram illustrating a possible pattern of holes within the support members.

Preferably, support members 7, 8, 9 and 10 are provided with a plurality of holes 16 therethrough so that connection can be made to spanning member 11 via the insertion of pins 17 through holes 16 of the support members 7, 8, 9 and 10 and through corresponding holes 18 located upon each lateral frame section 13 and 14. The height or dorso-ventral position, the cephalo-caudad position and the angular orientation of spanning member 11 can thus be adjusted by positioning holes 18 of spanning member 11 adjacent to appropriate holes 16 of support members 7, 8, 9, and 10 and inserting pins 17. Therefore, at least two holes 18 must be located upon each lateral frame section 13 and 14. To provide the greatest degree of flexibility in choice of angle of spanning member 11, however, multiple holes 18 are preferably provided in various positions upon lateral frame sections 13 and 14 (see FIG. 2). An example of a pattern of holes 16 within support members 7, 8, 9 and 10 is depicted schematically in FIG. 3. Of course, additional holes 16 could be provided to enable an even greater choice of angle, dorso-vential position and cephalo-caudad position.

The operator may thus adjust the angle of spanning member 11 as well as the gantry angle of the imaging system scanner to ensure that probe 4 lies in the angle of section. The angle of spanning member 11 may also be made adjustable by providing for a pivotal attachment of spanning member 11 to base 2. To minimize possible motion of spanning member 11 during invasive procedures, however, spanning member 11 is most preferably attached to support members 7, 8, 9 and 10 by insertion of pins 17 through holes 16. Attachment by pins also facilitates removal of the spanning member for sterilization or to enable unobstructed access to the patient.

Although it is preferable that support members 7, 8, 9 and 10 or other spanning member positioning means be attached to said base 2 as described above, the means for positioning spanning member 11 at the appropriate dorso-ventral position, cephalo-caudad position and angular orientation need not be attached to base 2.

Figure 4B:
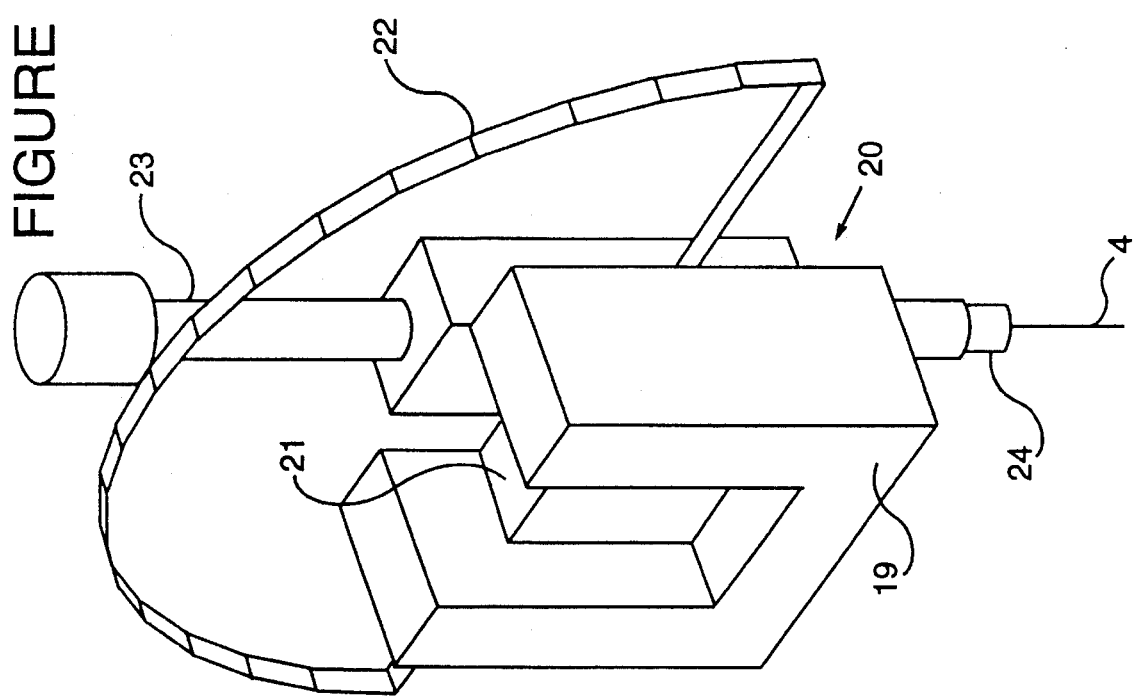
FIG. 4b is a rear prospective view of the probe holder with the protractor means adjacent thereto.
Figure 4A:
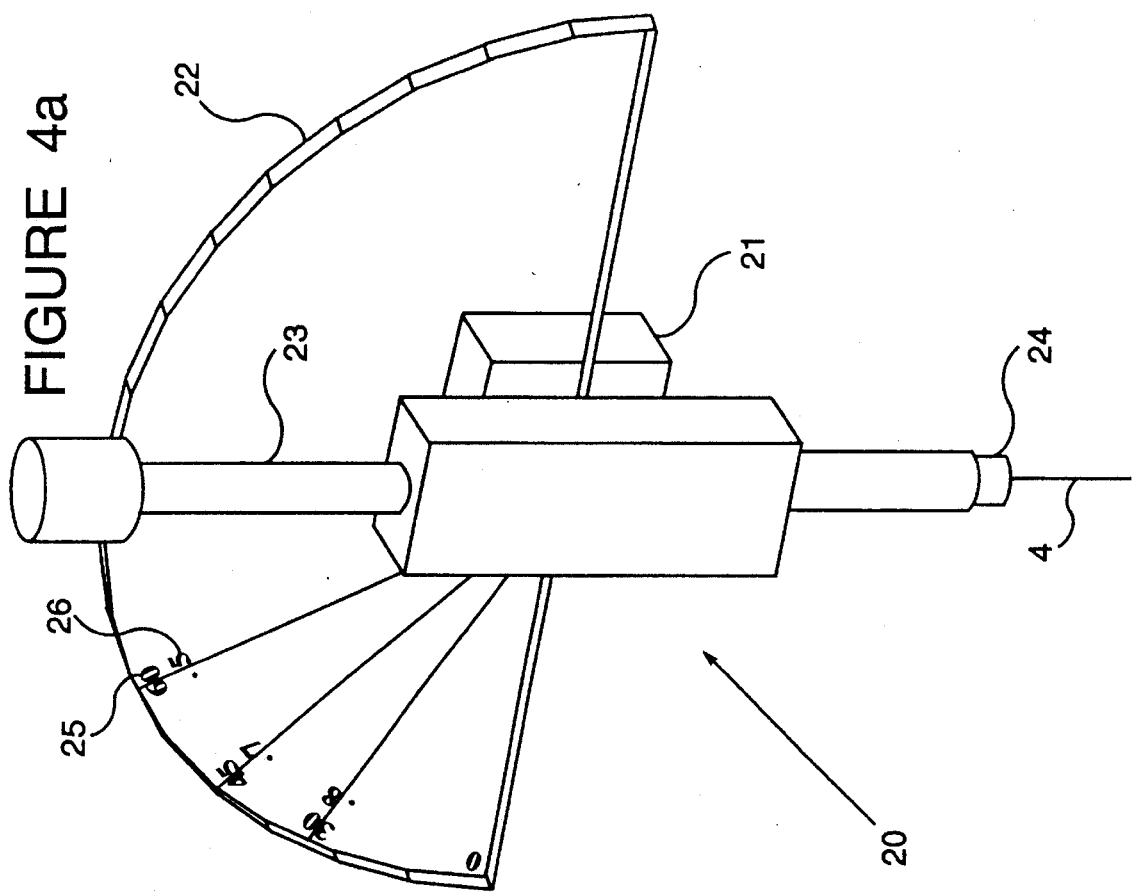
FIG. 4a illustrates the probe holder with the protractor means adjacent thereto.

Preferably, spanning frame section 12 is an arc-frame, but a flat frame can also be used. Preferably positioned on spanning member 11 are a plurality of receptacle means 19 through which a rotatable probe holder 20 can be attached to spanning frame member via frame attachment means 21 which operate connectively with receptacle means 19. FIG. 1 illustrates receptacle means 19 disposed only upon spanning frame section 12 of spanning member 11. Such receptacle means 19 may also be disposed upon lateral frame sections 13 and 14. Alternately, spanning member 11 can be designed so that the probe holder 20 can be slideably connected to spanning member 11, thereby providing the greatest degree of flexibility in probe holder position. Providing individual receptacle means 19 gives the greatest assurance of stability, however. Probe holder 20 and frame attachment means 21 are best illustrated in FIGS. 4a and 4b.

Rotatable probe holder 20 is preferably pivotally attached to frame attachment means 21 adjacent a protractor 22. Probe 4 such as a biopsy needle is preferably attached to a dowel 23 by positioning the hub 24 of probe 4 within the distal end of dowel 23. A sterile plastic interface (not shown) is preferably provide to both ensure sterility and a secure fit of probe 4 within dowel 23. This means of attaching probe 4 to dowel 23 also provides the operator with the ability to quickly release the probe 4 from dowel 23 at any time during needle placement.

Protractor 22 is provided with degree markings 25 and corresponding arc tangent markings 26 to enable immediate positioning of the dowel 23 (and thereby probe 4) to the appropriate angle of entry without the need for extensive calculation. For clarity, only a few such markings are depicted in FIG. 4a. In actual practice, sufficient markings would be provided to enable accurate positioning of the probe over a wide range of angles.

Stereotactic device 1 minimizes the axes of rotation necessary to achieve the desired orientation of probe 4, thereby reducing torsion within the system. This reduction in torsion enables highly accurate placement of probe 4. At a penetration depth of 23.0 cm., a degree of accuracy of less than 1.0 mm of variance is achievable. An accuracy of approximately 0.2 mm at a penetration depth of 23.0 cm is obtainable under conditions of ideal construction and homogeneous tissue.

Figure 5:
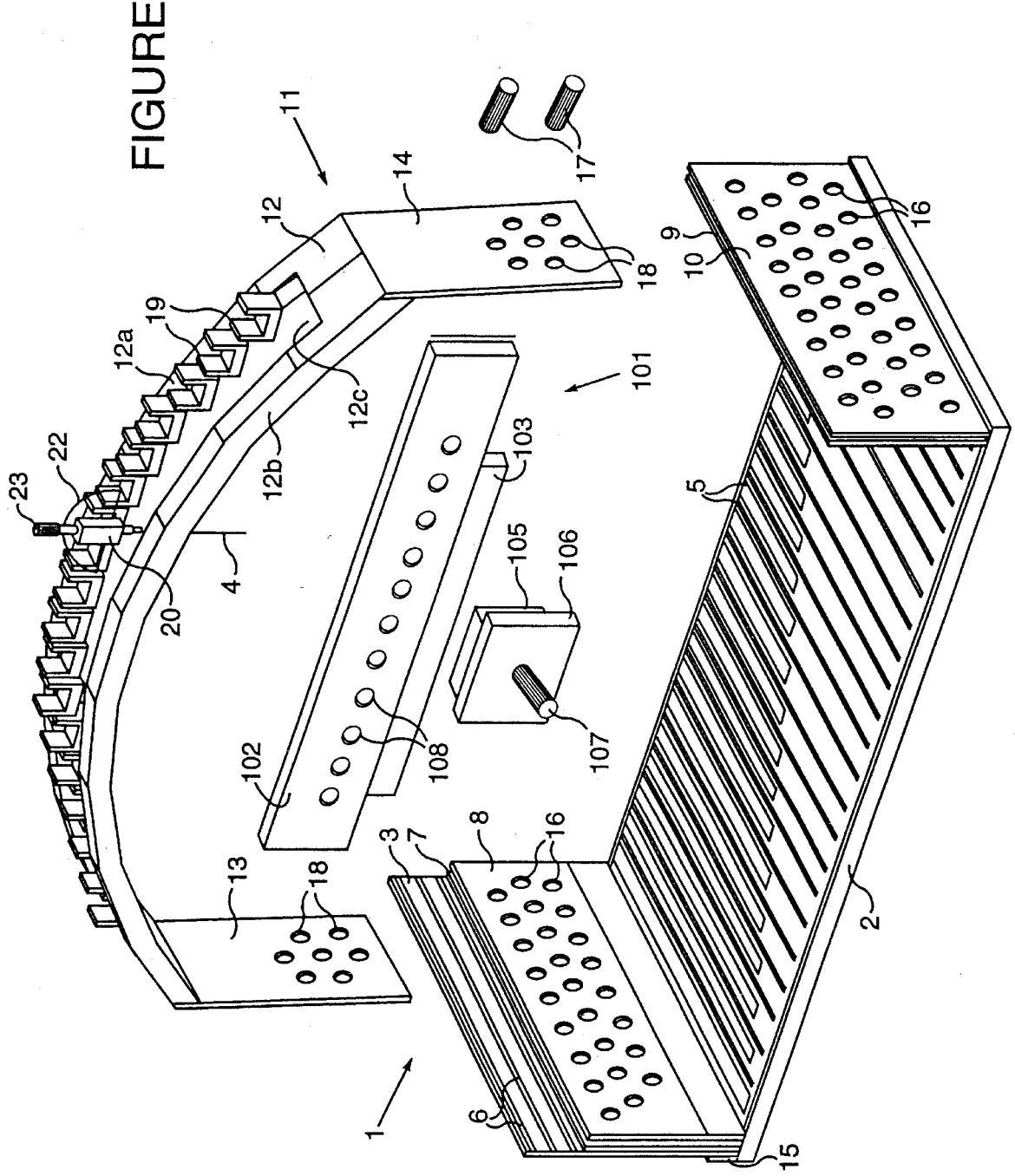
FIG. 5 is a right hand perspective view of the device illustrating the precompression means.
Figure 6:
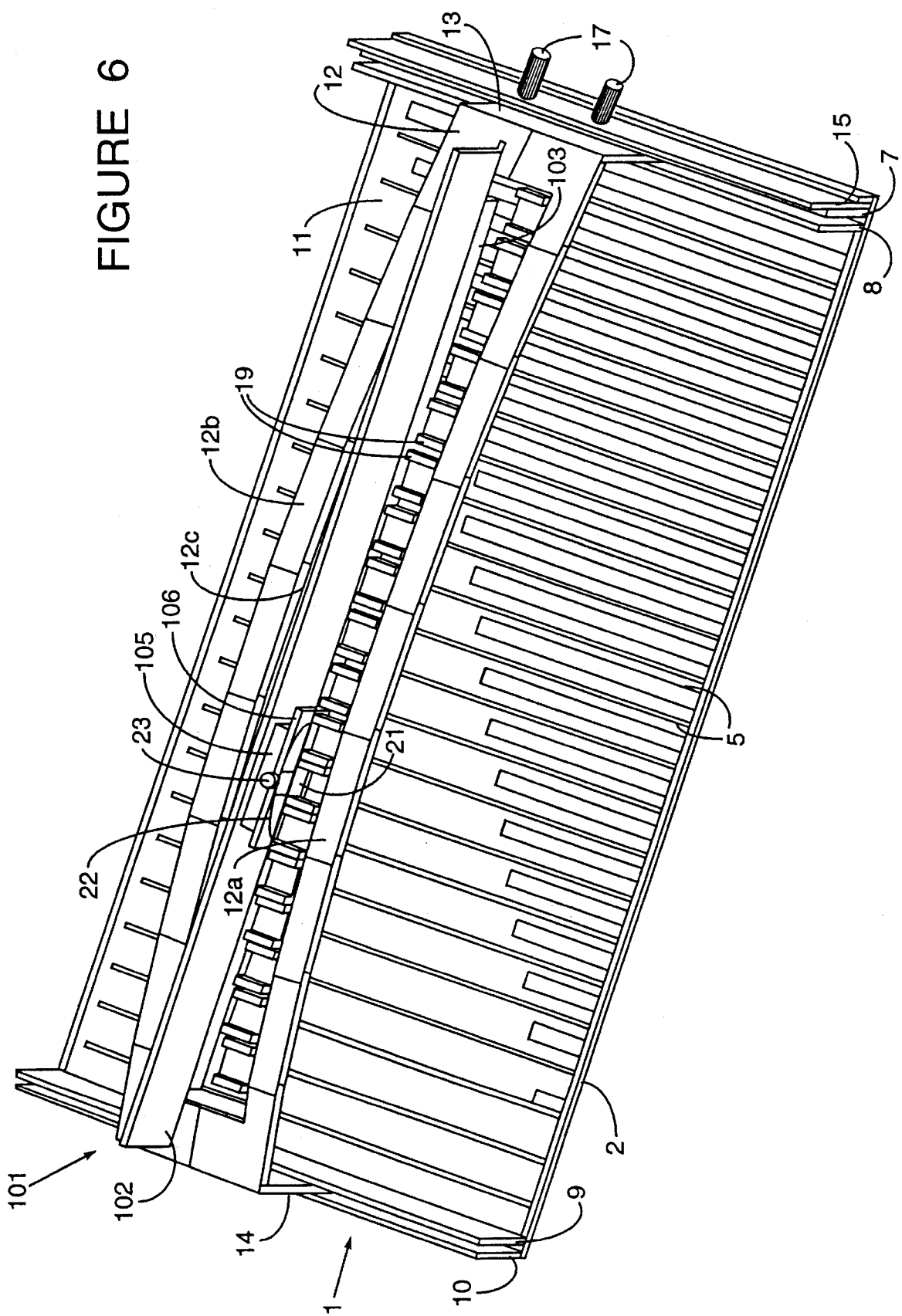
FIG. 6 is a top view of the device including the precompression means.

The present stereotactic device 1 also preferably includes one or more precompression means 101 preferably positioned adjacent the spanning member 11 enabling controlled compression of soft tissue during invasive procedures. Precompression means 101 or a portion thereof may be positioned adjacent the spanning frame section 12 and/or one or both of lateral frame sections 13 and 14 depending upon the location of the entry point of probe 4. A preferred embodiment of precompression means 101 is illustrated in FIGS. 5 and 6.

In this embodiment, spanning frame section 12 comprises two substantially parallel sections 12a and 12b separated by a distance to form a slot 12c therebetween. Receptacle means 19 are disposed in section 12a. Precompression means 101 is preferably designed to be disposed within slot 12c to be adjacent probe 4. Precompression means 101 preferably includes a support plate 102 and a compression plate 103. Compression plate 103 is preferably slideably disposed within or adjacent support plate 102.

A probe holder abutment means 104 is preferably provided to assist in maintaining the position of probe holder 20 relative to receptacle means 19 as well as to assist in maintaining the position of compression means 101 relative to probe holder 20. In the preferred embodiment illustrated in FIGS. 5 and 6, probe holder abutment means 104 comprises a rigid plate 105 and a compressible plate 106. Rigid plate 105 preferably abuts probe holder 20 while compressible plate 106 abuts compression means 101. Rigid plate 105 and compressible plate 106 are preferably attached to compression means 101 via insertion of a dowel 107 into an appropriate hole 108 disposed in support plate 102.

Compression means 101 and dowel holder abutment means 104, like stereotactic device 1 itself, are preferably constructed of materials substantially transparent to the form of energy used by the imaging system to generate the image. Compressible plate 106 is preferably constructed of a material of appropriate compressibility such that sufficient force is provided when compression means 101 and probe holder abutment means 104 are situated in slot 12c that probe holder 20 is firmly held within receptacle 19.

In operation, uniform force is applied to compression plate 103 to cause compression plate 103 to be driven downwards to compress the soft tissue in the area of the entry point of probe 4. The required uniform force can be provided by any means over which adequate control can be maintained, including electromechanical means or pneumatic means. Preferably, pneumatic means are used.

Figure 7:
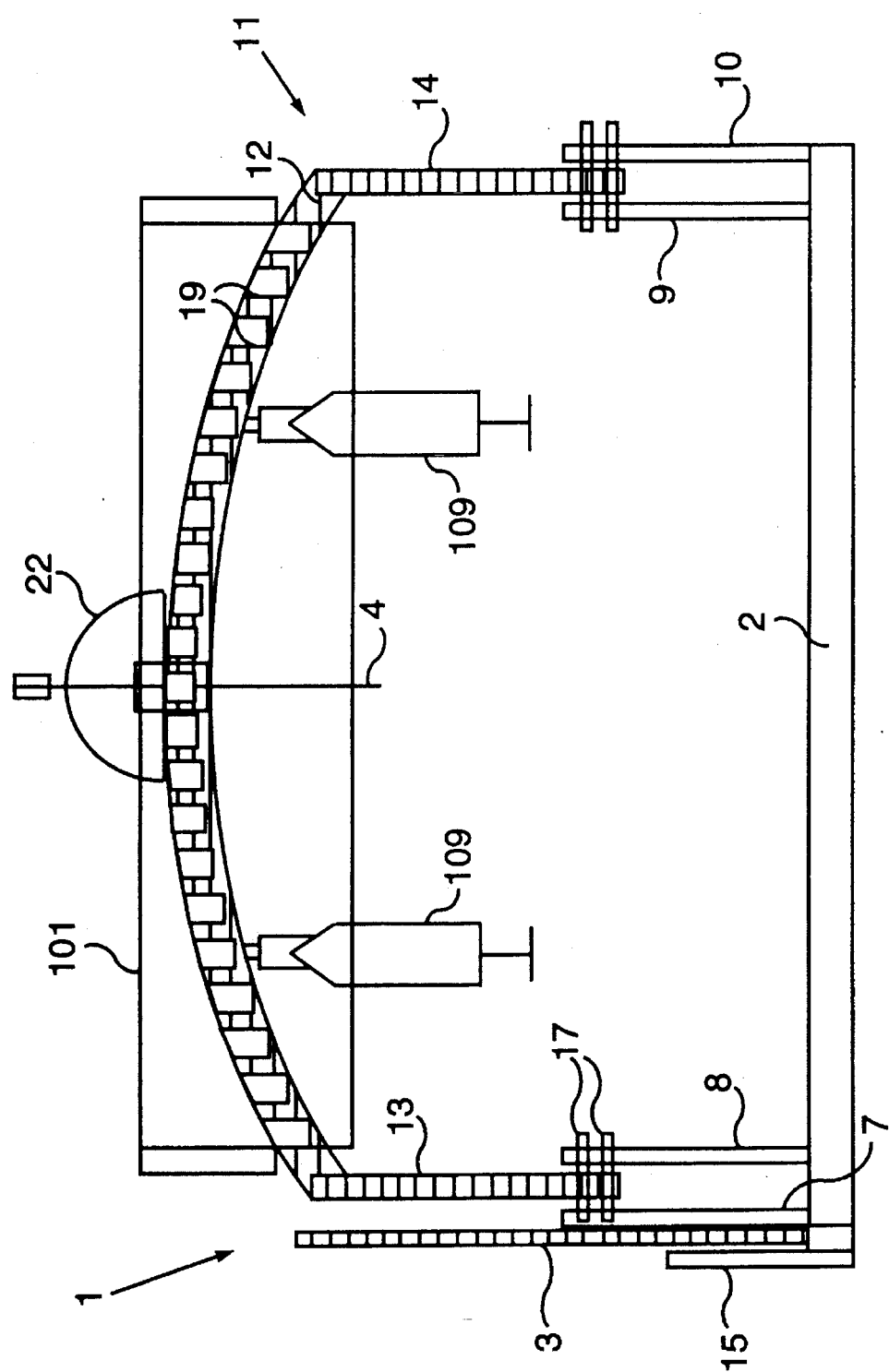
FIG. 7 is a side view of the device illustrating the precompression means and syringes.

In one embodiment, as depicted in FIG. 7, sterile syringes 109 are attached to the under-surface of spanning frame section 12 of spanning member 11 into operator-chosen, appropriate positions. The syringes are preferably connected to an air line (not shown) to provide simultaneous uniform pressure to drive the pistons of all syringes 109 equally. In this embodiment, it would be necessary to provide for pneumatic connection means (not shown) between spanning member 11 and compression means 101. Alternatively, sterile syringes 109 could be attached directly to compression means 101. Although syringes generally provide the most economical choice of a pneumatic compression device, other pneumatic compression devices can be used. A dedicated and more efficient pneumatic compression device, for example, can be used instead of syringes if application demands.

In the above-described embodiment, uniform pneumatic pressure is used to drive tissue compression plate 103 to compress the soft tissue in the area of the lesion. Alternatively, the uniform pressure can be used to inflate an inflatable bladder of appropriate shape and size to compress the soft tissue in the area of the lesion when inflated. Inflatable plastic rings or ovals can be provided with varying sizes to conform to different body sizes and biopsy/drainage locations.

Figure 8:
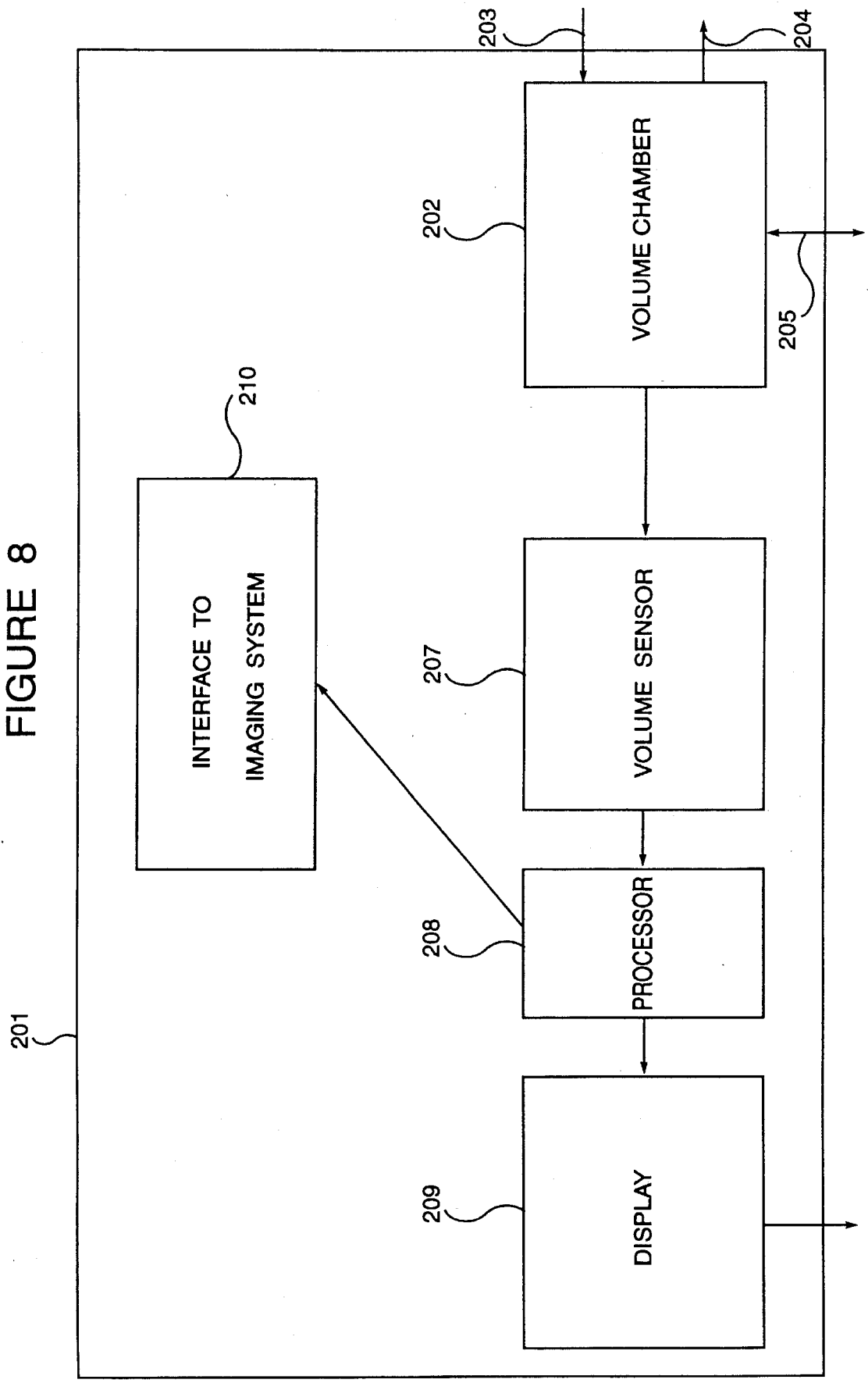
FIG. 8 is a schematic illustration of the respiration feedback means.

The present stereotactic device is also preferably provided with a respiratory feedback means 201 illustrated schematically in FIG. 8. Respiratory feedback means 201 is operable to enable the patient upon whom a diagnostic procedure or a biopsy or other interventional procedure is being performed to control the patient's degree of respiration. The effects of respiration on the diagnostic or interventional procedure can thereby be minimized.

By directly measuring respiratory volume and providing the appropriate feedback to the patient, every image can be obtained in the same phase of respiration. Thus, it is highly desirable to provide such feedback for use in conjunction with an imaging system during both diagnostic and interventional procedures. Several methods of measuring the volume of inspired or expired air are possible. The first preferred method involves using a chamber 202, preferably of fixed volume, as both the source of inspired air and the receptacle of expired air.

Chamber 202, as illustrated in FIG. 9, preferably includes an oxygen inlet 203 and an exhaust 204. A constant flow of oxygen is provided to the chamber via oxygen inlet 203. An equal amount of fluid is withdrawn from chamber 202 via exhaust 204. Absent any other extraneous influence upon chamber 202, the amount of fluid within chamber 202 will remain constant and a movable piston 205 disposed within chamber 202 will remain stationary. Chamber 202 is preferably kept under relatively isothermal conditions to remove the effect of temperature upon the volume of the fluid within the chamber.

Chamber 202 is also provided with respiration port 206 to which a patient can be respiratively connected. Upon inhalation by the patient, the resultant pressure reduction within chamber 202 causes movable piston 205 to move downwards. The change in volume is preferably measured by operatively connecting a sensor 207 such as an electromechanical conversion means to movable piston 205. An example of an appropriate electromechanical conversion means is a variable resistor. Alternatively, a pressure sensor can be used to measure the change in volume. Upon expiration, the resultant positive pressure will cause movable piston 205 to expand upwards.

In actual operation the respiratory feedback means 201 is preferably connected to the patient for an appropriate period of time to establish an adequate baseline. The volume of inspired air is measured and converted into an electrical signal of a voltage corresponding to the volume. The analog electrical signal is then converted to a digital signal and input to microprocessor 208 which subtracts a voltage corresponding to the amount of expired air as compared to the predetermined baseline.

Another method of measuring respiratory volume involves the placement of an air flow velocity gauge between the patient and the device. In this embodiment, however, the measurement of volume would be dependent upon flow, whereas in the first preferred embodiment, the measurement of volume is independent of flow.

Respiratory feedback means 201 also preferably comprises a display means 209 for displaying the information to the patient and preferably also the operator. Two preferable means of displaying the respiratory control information are through visual display and auditory signalling. The visual display preferably comprises a panel of small LEDs or other visual display which indicate not only the baseline volume, but also the degree of deviation from that volume in both the inspiratory and expiratory direction. Alternatively, this information can be conveyed by auditory signalling. In the auditory signalling method, a certain frequency signal is emitted corresponding to the desired volume. A second frequency signal variably adjustable to represent the patient's actual respiration is also emitted. When the two signal frequencies match, respiration is at the desired volume. Tactile feedback, such as vibration or thermal feedback, is also possible.

The display of information should thus include an indication of the baseline point and an indication of the variance from the baseline on inspiration and expiration. Furthermore, the information is preferably displayed on each image of the imaging system for diagnostic and biopsy/draining procedural purposes. Respiratory feedback means 201 is thus preferably provided with an interface means 210 for providing the information to the imaging system. The interface means 210 can be a computer or electrical interface to enable direct communication between the processor 208 of the respiratory feedback means 201 and the software of the imaging system. This embodiment is depicted in FIG. 8. Alternatively a physical indicator of respiratory volume could be placed in respiratory connection with the patient and positioned within the image plane of the imaging system. An example of such physical indicator is a vial or other container containing a fluid of appropriate radiodensity. The position of the fluid within the vial would correspond to the respiratory volume. The interface means 210 enables the reproduction and confirmation of the phase of respiration on each image obtained for biopsies and drainages as well as for diagnostic purposes.

Method of Operation of Stereotactic Device in Biopsy Usms CT or MRI Guidance

In the operation of the present stereotactic device, the patient is first positioned on the CT or MRI table (not shown), lying on top of base 2 of device 1. The known lesion is placed approximately in the mid portion of localization grid 5 of the base 2. For the localization and in-plane translation and rotation of probe 4 to be possible, it is very important that the plane of stereotactic device 1 be aligned precisely with the plane of the image. Since the position of the lesion will be determined with respect to device 1, the positioning of base 2 with respect to the horizontal and vertical are not critical. It is critical, however, that the planar axes of device 1 as defined by the angle of spanning member 11 in relation to base 2 correspond to the plane of the scan image. If there is any deviation, translation of needle 4 will cause the needle tip to deviate from the image plane. In an axial CT scan, for example, the edge of the gantry is preferably aligned perpendicularly to the image plane. Therefore, if base member 2 is aligned parallel to the gantry table and spanning member 11 is placed in a vertical position, the plane of the device and the image will coincide.

Localization grid 6 of localizing side member 3 is preferably attached to base 2 on one side of the patient. A CT or MRI scan is then performed to determine the position of the lesion. Both the cephalo-caudad and dorso-ventral position of the lesion are identified by both the CT or MRI software "electronic caliphers" and the alternating radiopaque bars and wires of base localization grid 5 and side localization grid 6 of the device 1.

Following localization, localizing side member 3 is removed to position overlying arc-frame spanning member 11 at the appropriate cephalo-caudad level and angle of orientation. Localizing side member 3 is then reattached to base 2. The height of spanning frame section 12 is positioned using pins 17 so that the distance between spanning frame section 12 and the patient's skin is minimized. Minimization of the distance between spanning frame section 12 and the patient's skin minimizes the total distance of travel required of probe 4 and thereby minimizes possible error in placement.

From a single image in the plane of the lesion, the desired angle and the distance from skin entry to lesion can be determined by the user.

Using radiopaque base localization grid 5 and radiopaque side localization grid 6, the tangent of the desired angle of penetration means 4 can be calculated by dividing the depth in the dorso-ventral direction by the lateral distance in the left-right direction. The angle tangent allows the angle of biopsy to be easily adjusted using the arc-tangent markings 26 on protractor 22 of device 1. If necessary, the angle can be recalculated at any time, especially if compression is desired.

Use of Compression

After preparing the skin surface in the procedure area, sterile syringes 109 or other compression means can be attached to the under surface of spanning frame section 12 into operator chosen appropriate positions. The syringes 109 or other compression means are preferably attached to the underside of spanning frame section via matching threads of a standardized size (not shown). After the syringes are attached, a master syringe (not shown) is connected to the air lines (not shown) on both halves of spanning frame section 12 and is used to simultaneously provide uniform pressure to drive the pistons of all syringes 109 equally. The uniform pressure is used to drive a precompression means 101 including a compression plate 103 or alternatively to inflate a bladder to compress soft tissue in the area of the entry point of the probe 4.

Performing the Biopsy or Other Invasive Procedure

Using sterile technique, the operator wraps the tip of biopsy dowel 23 with a sterile plastic covering. The distal end of biopsy dowel 23 fits over hub 24 of sterile probe 4. Since biopsy needle designs vary, the device is preferably designed to accommodate more than one configuration of dowel 23 including coaxial systems used in conjunction with various automated biopsy systems. The hub 24 of the probe or needle 4 is positioned within the dowel 23 preferably with a sterile plastic sheet acting as an interface. The operator advances the tip of the probe or needle 4 from the skin to the target lesion at the previously determined angle and distance. The respiratory control means 201 standardizes breathing positional changes.

The user performs the needle advancement in a very specific manner. The biopsy dowel 23 is grasped using a sterile plastic covering and is used for loading in the orientation of the plane of the image only. The physician's other hand may be utilized for reducing potential needle buckling without lateral or cephalo-caudad deviation. In this manner, biopsy device 1 provides continuous guidance of the probe or needle 4 without operator-induced error.

The biopsy can be performed by currently known techniques including aspiration or spring-loaded core biopsy gun. Device 1 accommodates all standard procedures.

Because spanning member 11 is designed to operate within the plane of the imaging system section, images accurately reflecting the probe position can be obtained at any time. Additional images can also be performed to position additional probes or check for complications such as local hemorrhage. For safety, the biopsy dowel 23 can be immediately disengaged and the probe 4 removed whenever required. Following performance of the biopsy, the specimen is delivered to the pathologist.

While presently preferred embodiment of the invention have been disclosed and described in particularity, the invention may be otherwise embodied with in the scope of the appended claims.

What is claimed is:

1. A stereotaxic localization system for use in conjunction with an imaging system, comprising:
   a. A respiratory feedback device in which respiratory volume is directly measured to define a phase of respiration of a patient, said phase of respiration providing an indication of the position of internal organs of the patient, said respiratory feedback device comprising:
      i. A chamber, said chamber comprising a respiration port for respirative connection with the patient;
      ii. A volume sensor means in communicative connection with said chamber; and
      iii. A display means for displaying respiratory volume to the patient, said display means being in operative connection with said volume sensor means, whereby respiratory volume at a particular time is displayed to the patient to allow the patient to actively control respiratory volume and thereby the position of the patients internal organs; and
   b. A stereotaxic localization means for placing a probe at a desired location within a body during a known phase of respiration as determined by said respiratory feedback device.

2. The stereotaxic localization system of claim 1 wherein said chamber has a movable piston disposed therein, said volume sensor means being in operative connection with said movable piston.

3. The stereotaxic localization system of claim 2 wherein said chamber further comprises:
   a. An oxygen inlet; and
   b. An exhaust, wherein an inflow rate of oxygen into said chamber is substantially the same as an outflow rate of gas exiting said exhaust.

4. The stereotaxic localization system of claim 1 further comprising a means for interfacing said respiratory feedback device to the imaging system, said interface means being in communicative connection with said volume sensor means to enable display of the phase of respiration upon a display of the imaging system.

5. The stereotaxic localization system of claim 4 wherein said interface means comprises an electrical interface suitable for effecting electrical connection between said respiratory feedback device and the imaging system.

6. The stereotaxic localization system of claim 1 further comprising a computer processing unit in communicative connection with said volume sensor means, said computer processing unit being operable to process data from said volume sensor means.

7. A stereotaxic localization system for use in conjunction with an imaging system, comprising:
   a. A respiratory feedback device in which respiratory volume is directly measured to define a phase of respiration of a patient, said phase of respiration providing an indication of the position of internal organs of the patient, said respiratory feedback device comprising:

i. A chamber, said chamber comprising a respiration port for respirative connection with the patient;

ii. A volume sensor means in communicative connection with said chamber; and iii. A display means for displaying respiratory volume to the patient, said display means being in operative connection with said volume sensor means, whereby respiratory volume at a particular time is displayed to the patient to allow the patient to actively control respiratory volume and thereby the position of the patient's internal organs; and iv. A reference means for indicating the phase of respiration, said reference means comprising a physical representation of respiratory volume placeable within an image plane of the imaging system, said physical representation of respiratory volume being constructed to appear upon the display of the imaging system; and b. A stereotaxic localization means for placing a probe at a desired location within a body during a known phase of respiration as determined by said respiratory feedback device.

8. The stereotaxic localization system of claim 7 further comprising a computer processing unit in communicative connection with said volume sensor means, said computer processing unit being operable to process data from said volume sensor means.

9. An improved method of performing an imaging-system procedure using an imaging system, the improvement comprising the steps of directly measuring the respiratory volume of a patient to define a phase of respiration of the patient, said phase of respiration providing an indication of the position of internal organs of the patient, providing information regarding the phase of respiration to the patient to enable the patient to control the phase of respiration, and performing a scan with the imaging system to produce an image, the phase of respiration being identified through measurement of the respiratory volume of the patient at the time the image is displayed with the imaging system.

10. The method according to claim 9 wherein the respiratory volume is measured by measuring the position of a movable piston within a constant volume chamber, said chamber being in respirative connection with the patient.

11. The method according to claim 9 wherein the respiratory volume is measured by placing an air flow velocity gauge in respirative connection to the patient.

12. The method according to claim 9 further comprising the step of displaying the information regarding the phase of respiration upon a display of the imaging system.

13. The method according to claim 9 further comprising the step of establishing a respiration baseline as a reference.

14. The method according to claim 13 further comprising the step of displaying the information regarding the phase of respiration and the respiration baseline upon a display of the imaging system.

15. A stereotaxic localization system for use in conjunction with an imaging system, comprising:

a. A respiratory feedback device in which respiratory volume is directly measured to define a phase of respiration of a patient, said phase of respiration providing an indication of the position of internal organs of the patient, said respiratory feedback device comprising:

i. A volume sensor means, said volume sensor means comprising a respiration port for respirative connection with the patient; and ii. A display means for displaying respiratory volume to the patient, said display means being in operative connection with said volume sensor means, whereby the respiratory volume at a particular time is displayed to the patient to allow the patient to actively control the respiratory volume and thereby the position of the patient's internal organs; and b. A stereotaxic localization means for placing a probe at a desired location within a body during a known phase of respiration as determined by said respiratory feedback device.

16. The stereotaxic localization system of claim 15 wherein said volume sensor means comprises a flow velocity gauge.

17. The stereotaxic localization system of claim 15 further comprising a means for interfacing said respiratory feedback means to the imaging system, said interface means enabling display of the phase of respiration upon a display of the imaging system.

18. The stereotaxic localization system of claim 17 wherein said interfacing means comprises an electrical interface suitable for effecting electrical connection between said respiratory feedback device and the imaging system.

19. The stereotaxic localization system of claim 15 further comprising a computer processing unit in communicative connection with said volume sensor means, said computer processing unit being operable to process data from said volume sensor means.

20. A stereotaxic localization system for use in conjunction with an imaging system, comprising:

a. A respiratory feedback device in which respiratory volume is directly measured to define a phase of respiration of a patient, said phase of respiration providing an indication of the position of internal organs of the patient, said respiratory feedback device comprising:

i. A volume sensor means, said volume sensor means comprising a respiration port for respirative connection with the patient;

ii. A display means for displaying respiratory volume to the patient, said display means being in operative connection with said volume sensor means, whereby respiratory volume at a particular time is displayed to the patient to allow the patient to actively control respiratory volume and thereby the position of the patient's internal organs; and iii. A reference means for indicating the phase of respiration, said reference means comprising a physical representation of respiratory volume placeable within an image plane of said imaging system, said physical representation being constructed to appear upon a display of the imaging system; and b. A stereotaxic localization means for placing a probe at a desired location within a body during a known phase of respiration as determined by said respiratory feedback device.

21. The stereotaxic localization system of claim 20 further comprising a computer processing unit in communicative connection with said volume sensor means, said computer processing unit being operable to process data from said volume sensor means.

\* \* \* \* \*